(12) United States Patent
Dakka et al.

(10) Patent No.: US 8,222,459 B2
(45) Date of Patent: Jul. 17, 2012

(54) PROCESS FOR PRODUCING CYCLOHEXANONE

(75) Inventors: Jihad M. Dakka, Whitehouse Station, NJ (US); John S. Buchanan, Lambertville, NJ (US); James R. Lattner, LaPorte, TX (US); Sadi Mizrahi, Houston, TX (US)

(73) Assignee: Exxonmobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/933,700

(22) PCT Filed: Feb. 19, 2009

(86) PCT No.: PCT/US2009/034514
§ 371 (c)(1),
(2), (4) Date: Sep. 21, 2010

(87) PCT Pub. No.: WO2009/134514
PCT Pub. Date: Nov. 5, 2009

(65) Prior Publication Data
US 2011/0021844 A1    Jan. 27, 2011

Related U.S. Application Data

(60) Provisional application No. 61/049,540, filed on May 1, 2008.

(30) Foreign Application Priority Data

Jun. 19, 2008   (EP) .................................... 08158572

(51) Int. Cl.
C07C 45/00 (2006.01)
(52) U.S. Cl. ........................ 568/346; 568/361
(58) Field of Classification Search ................ 568/346, 568/361
See application file for complete search history.

(56) References Cited

U.S. PATENT DOCUMENTS

| | | | |
|---|---|---|---|
| 2,291,585 A | 7/1942 | Bartlett et al. | |
| 3,076,810 A | 2/1963 | Duggan et al. | |
| 3,194,843 A | 7/1965 | Silber et al. | |
| 3,358,044 A | 12/1967 | Russell et al. | |
| 3,442,958 A | 5/1969 | Choo | |
| 3,514,492 A | 5/1970 | Juguin et al. | |
| 3,519,575 A | 7/1970 | Bozik et al. | |
| 3,534,110 A | 10/1970 | Juguin et al. | |
| 3,534,116 A | 10/1970 | Fuller | |
| 3,580,970 A | 5/1971 | Swift | |
| 3,691,102 A | 9/1972 | Swift | |
| 3,775,487 A | 11/1973 | Isbitsky, Jr. et al. | |
| 4,162,267 A | 7/1979 | Fisher et al. | |
| 4,167,456 A | 9/1979 | Murtha | |
| 4,169,857 A | 10/1979 | Murtha | |
| 4,328,372 A | 5/1982 | Wu | |
| 4,417,076 A | 11/1983 | Rozovsky et al. | |
| 4,520,129 A | 5/1985 | Murtha | |
| 4,929,762 A | 5/1990 | Matsunaga et al. | |
| 4,933,507 A | 6/1990 | Inoki et al. | |
| 5,256,348 A | 10/1993 | Waller | |
| 5,292,960 A | 3/1994 | Miere et al. | |
| 5,395,976 A | 3/1995 | Scharschmidt et al. | |
| 6,037,513 A | 3/2000 | Chang et al. | |
| 6,376,422 B1 | 4/2002 | McNabb et al. | |
| 7,285,512 B2 | 10/2007 | Bai et al. | |
| 7,285,685 B2 | 10/2007 | Walsdorff et al. | |
| 7,396,798 B2 | 7/2008 | Ma et al. | |
| 7,538,066 B2 | 5/2009 | Soled et al. | |

FOREIGN PATENT DOCUMENTS

| | | |
|---|---|---|
| FR | 1509921 | 1/1968 |
| FR | 1541720 | 10/1968 |
| GB | 986 931 | 3/1965 |
| JP | 06-263668 | 9/1994 |
| JP | 07-188082 | 7/1995 |
| JP | 2637812 | 8/1997 |
| WO | 01/74767 | 10/2001 |
| WO | 2008/128638 | 10/2008 |
| WO | 2010/024975 | 3/2010 |

OTHER PUBLICATIONS

Saito, Y., et al. "Performance of activity test on supported Pd catalysts for dehydrogenation of cyclohexanone to phenol (effect of supports on activity)", Ibaraki Kogyo Koto Senmon Gakko Kenkyu Iho (1995), vol. 30, pp. 39-46—English Abstract Only.
Swift, H. et al., "Metallic Phases and Activites of Nickel-Tin-Silica Catalysts Dehydrogenation of Cyclohexanone, Cyclohexanol, and Cyclohexane", Journal of Catalysis, 1968, vol. 12, pp. 5-14.
Milczanowski, S., et al., "Catalytic Dehydrogenation of Cyclohexanone to Phenol", PrZEMYSL Cheniczny, 1978, vol. 57, No. 3, pp. 129-130—English Abstract Only.
Waligora, B., et al., Waligora, B., et al., "Catalytic Dehydrogenation of Mixture of Cyclohexanol and Cyclohexanon to Phenol", Prace Chemiczne, 1982, vol. 27, pp. 93-99—English Abstract Only.
Arends, I., et al., "Selective Catalytic Oxidation of Cyclohexylbenzene to Cyclohexylbenzene-1-Hydroperoxide: A Coproduct-Free Route to Phenol" Tetrahedron, 2002, vol. 58, pp. 9055-9061.

Primary Examiner — Sikarl Witherspoon
(74) Attorney, Agent, or Firm — Jamie L. Sullivan

(57) ABSTRACT

In a process for producing cyclohexanone, cyclohexylbenzene is oxidized to produce cyclohexylbenzene hydroperoxide and then the resultant cyclohexylbenzene hydroperoxide is cleaved to produce an effluent stream comprising phenol and cyclohexanone. At least a portion of the effluent stream is then fed to at least one hydrogenation reaction zone, where the effluent stream portion is contacted with hydrogen in the presence of a hydrogenation catalyst under conditions effective to convert at least part of the phenol in the effluent portion into cyclohexanone.

12 Claims, No Drawings

PROCESS FOR PRODUCING CYCLOHEXANONE

CROSS-REFERENCE TO RELATED APPLICATIONS

This application is a National Stage Application of International Application No. PCT/US2009/034514 filed Feb. 19, 2009, which claims priority from U.S. Ser. No. 61/049,540 filed May 1, 2008, both of which are incorporated herein by reference.

FIELD OF THE INVENTION

The present invention relates to a process for producing cyclohexanone.

BACKGROUND

Cyclohexanone is an important product in the chemical industry and is useful as, for example, an industrial solvent, as an activator in oxidation reactions and in the production of adipic acid, cyclohexanone resins, cyclohexanone oxime, caprolactam and nylon 6.

Currently, the most common route for the production of cyclohexanone is by oxidation of cyclohexane to cyclohexyl hydroperoxide, which is then cleaved to produce cyclohexanol and cyclohexanone in substantially equimolar amounts.

Another potential route for the production of cyclohexanone is by a variation of the Hock process, in which benzene is converted to cyclohexylbenzene and the cyclohexylbenzene is oxidized to produce cyclohexylbenzene hydroperoxide, which is then cleaved to produce cyclohexanone and phenol in substantially equimolar amounts. This route has the potential advantage that phenol is a highly valued intermediate in the production of phenolic resins, bisphenol A, ϵ-caprolactam, adipic acid, and plasticizers.

One problem in producing phenol by way of the cleavage of cyclohexylbenzene hydroperoxide is that the cyclohexanone and phenol form an azeotropic mixture composed of 28 wt % cyclohexanone and 72 wt % phenol. Thus any attempt to separate the cleavage effluent by simple distillation results in this azeotropic mixture. Moreover, any unreacted cyclohexylbenzene in the cleavage effluent will co-distill with the azeotropic mixture. A further potential problem with the cyclohexylbenzene route to cyclohexanone is that, although both phenol and cyclohexanone are valuable commodities with growing markets, it would be useful to have a technology for balancing the supply and demand between these two products.

The present invention seeks to address these problems by providing a process for producing cyclohexanone by oxidation of cyclohexylbenzene to cyclohexylbenzene hydroperoxide followed by cleavage of the cyclohexylbenzene hydroperoxide, in which at least a portion of the effluent from the cleavage step is subjected to a selective hydrogenation step. The hydrogenation step converts at least part of the phenol in the effluent portion to additional cyclohexanone. Although the cleavage effluent portion subjected to the hydrogenation step can be a substantially pure phenol fraction separated from the raw effluent, given the cost of this separation, the process can also be applied to an effluent portion containing some or all of the cyclohexanone produced in the cleavage step. In this way, the total cost of purifying the final cyclohexanone stream and, if present, the final phenol stream can be minimized. Then, depending on the then current demand for phenol, part or all of the cyclohexanone could be dehydrogenated back to phenol. Alternatively, all the cyclohexanone could be recovered as saleable product.

SUMMARY

In one aspect, the invention resides in a process for producing cyclohexanone, the process comprising:
(a) oxidizing cyclohexylbenzene to produce cyclohexylbenzene hydroperoxide;
(b) converting cyclohexylbenzene hydroperoxide from (a) to produce an effluent stream comprising phenol and cyclohexanone;
(c) feeding at least a portion of said effluent stream to at least one hydrogenation reaction zone; and
(d) contacting said effluent stream portion with hydrogen in the presence of a hydrogenation catalyst in said hydrogenation reaction zone under conditions effective to convert at least part of the phenol in said effluent portion into cyclohexanone.

In one embodiment, said effluent stream portion fed to said hydrogenation reaction zone has the same composition as the effluent stream produced by said converting (b).

In another embodiment, the process further includes subjecting the effluent stream produced by said converting (b) to at least one separation step such that said effluent stream portion fed to said dehydrogenation reaction zone contains less cyclohexanone than the effluent stream producing by said converting (b).

Conveniently, the conditions in (d) comprise a temperature of about 20° C. to about 250° C. and/or a pressure of about 101 kPa to about 10,000 kPa and/or a hydrogen to phenol molar ratio of about 1:1 to about 100:1.

Conveniently, the hydrogenation catalyst comprises platinum and/or palladium.

In a further aspect, the invention resides in a process for producing cyclohexanone, the process comprising:
(1) contacting benzene and hydrogen with a catalyst under hydroalkylation conditions to produce cyclohexylbenzene;
(2) oxidizing cyclohexylbenzene from (1) to produce cyclohexylbenzene hydroperoxide;
(3) converting cyclohexylbenzene hydroperoxide from (2) to produce an effluent steam comprising phenol and cyclohexanone;
(4) feeding at least a portion of said effluent stream to at least one hydrogenation reaction zone; and
(5) contacting said effluent stream portion with hydrogen in the presence of a hydrogenation catalyst in said hydrogenation reaction zone under conditions effective to convert at least part of the phenol in said effluent portion into cyclohexanone.

It will be understood that the above further aspect of the invention constitutes an embodiment where steps (2), (3), (4) and (5) correspond to previously stated process steps (a), (b), (c) and (d), respectively. However, in this embodiment the cyclohexylbenzene oxidized in step (2) has been produced by hydroalkylation of benzene according to step (1). Thus, step (1) may be considered as an optional cyclohexylbenzene feedstock-producing step that, in a preferred embodiment, precedes step (a). Alternatively stated, in a preferred embodiment the process of the invention comprises a preliminary step of contacting benzene and hydrogen with a catalyst under hydroalkylation conditions to produce the cyclohexylbenzene for oxidizing in step (a).

DETAILED DESCRIPTION OF THE EMBODIMENTS

Described herein is a process for producing cyclohexanone from cyclohexylbenzene that allows the co-produced phenol to be partially or totally converted to additional cyclohexanone. In the present process, cyclohexylbenzene, which in a preferred embodiment is produced by the catalytic hydroalkylation of benzene, is oxidized to produce cyclohexylbenzene hydroperoxide and then the cyclohexylbenzene hydroperoxide is cleaved to produce an effluent stream comprising phenol and cyclohexanone in substantially equimolar amounts. At least a portion of the effluent stream is then fed to a hydrogenation reaction zone, where the effluent stream portion is contacted with hydrogen in the presence of a hydrogenation catalyst and under conditions effective to convert the cyclohexanone in said effluent portion into additional phenol.

Production of Cyclohexylbenzene

The cyclohexylbenzene employed in the present process can be produced by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice it is preferred that the cyclohexylbenzene is generally produced by contacting benzene with hydrogen under hydroalkylation conditions in the presence of a hydroalkylation catalyst whereby the benzene undergoes the following reaction (I) to produce cyclohexylbenzene (CHB):

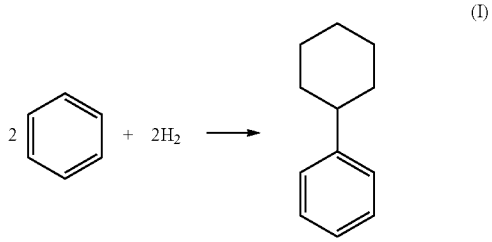

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm by weight, water and/or less than 100 ppm, such as less than 30 ppm, for example less than 3 ppm by weight, sulfur and/or less than 10 ppm, such as less than 1 ppm, for example less than 0.1 ppm by weight, nitrogen.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C. Suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is preferably a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures of any two or more thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst although suitable metals include palladium, ruthenium, nickel, zinc, tin and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and particularly preferably substantially all (eg at least 95, 98 or 99 wt %) or even 100 wt % of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina and/or titania and/or zirconia. As used herein, the numbering scheme for the Periodic Table Groups is as disclosed in Chemical and Engineering News, 63(5), 27 (1985).

The hydrogenation metal is conveniently deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

The catalyst may also comprise a binder. For such catalysts, the binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain some dialkylated products, as well as unreacted aromatic feed and the desired monoalkylated species. The unreacted aromatic feed is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y or mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

Cyclohexylbenzene Oxidation

In order to convert the cyclohexylbenzene into phenol and cyclohexanone, the cyclohexylbenzene is initially oxidized to the corresponding hydroperoxide. This may be accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-trihydroxyisocyanuric acid.

These catalytic materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount of from 0.0001 mol % to 15 mol %, such as from 0.001 to 5 mol %, of the cyclohexylbenzene.

Suitable conditions for the oxidation step include a temperature between about 70° C. and about 200° C., such as about 90° C. to about 130° C., and/or a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of for example about 20° C. to about 150° C., such as about 40° C. to about 120° C., and/or a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

Post Treatment of Cleavage Effluent

The effluent from the cleavage reaction comprises phenol and cyclohexanone in substantially equimolar amounts. The present process provides an advantageous route to increasing the amount of cyclohexanone produced from the original benzene feed by contacting at least part of the cleavage effluent with hydrogen in the presence of a hydrogenation catalyst so as to convert some or all of the phenol in the effluent into additional cyclohexanone according to the reaction (II):

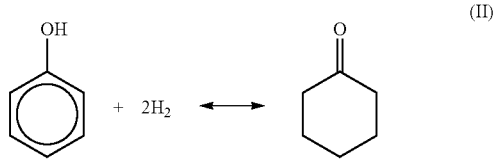

Any suitable hydrogenation catalyst can be used in reaction (II), such as, for example, a platinum or palladium catalyst. Similarly the hydrogenation conditions do not have to be closely controlled. They typically comprise a temperature of about 20° C. to about 250° C. and/or a pressure of about 101 kPa to about 10,000 kPa and/or a hydrogen to phenol molar ratio of about 1:1 to about 100:1. The hydrogenation reaction can be conducted in a wide range of reactor configurations including fixed bed, slurry reactors, and/or catalytic distillation towers.

In one embodiment, an activated palladium catalyst, such as that described in U.S. Pat. No. 5,395,076, is employed. Preferably the conditions for the hydrogenation step comprise a temperature of about 150° C. to about 250° C. and/or a pressure of about 0.8 to about 8 bar (80 kPa to 800 kPa), and/or a hydrogen to phenol molar ratio of about 3.5:1 to about 10:1. The catalyst is preferably activated with hydrogen-containing gases, in particular hydrogen/nitrogen mixtures, or with pure hydrogen. Such activation may be, for example for about 50 hours to about 10 hours at for example about 300° C. to about 500° C., preferably for 40 hours to 20 hours at for example about 350° C. to about 450° C., more preferably for about 35 to about 20 hours at for example about 370° C. to about 450° C. It has been found that by employing such activation, the hydrogenation may proceed with high selectivity to cyclohexanone, such that the molar ratio of cyclohexanone to cyclohexanol in the product is for example between 85:15 and 98:2.

As previously stated, cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. However, the efficiency of the separation can be enhanced by conducting the distillation under at least partial vacuum, typically at below 101 kPa.

Moreover, extractive distillation processes are known for separating cyclohexanone and phenol, see for example, U.S. Pat. Nos. 4,021,490, 4,019,965, 4,115,207, 4,115,204, 4,115,206, 4,201,632, 4,230,638, 4,167,456, 4,115,205, and 4,016,049. Nevertheless, phenol/cyclohexanone separation remains a costly process, so that in one embodiment, the feed to the hydrogenation step has the same composition as the cleavage effluent, thereby avoiding the need for an initial expensive separation step. Depending on the efficiency of the phenol hydrogenation, the final product may be substantially free of phenol, thereby at least reducing the problem of separating the phenol from the cyclohexanone in the cleavage effluent.

In another embodiment, the cleavage effluent is subjected to one or more separation processes to recover or remove one or more components of the effluent prior to hydrogenation. In particular, the cleavage effluent is conveniently subjected to at least a first separation step to recover some or all of the cyclohexanone from the effluent, typically so that the effluent stream fed to the hydrogenation reaction contains less than 50 wt %, for example less than 30 wt %, such as from 0.5 to 20 wt %, and particularly less than 1 wt %, cyclohexanone. The first separation step is conveniently effected by vacuum distillation and the same, or additional vacuum distillation steps, can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the hydrogenation reaction.

By employing the present hydrogenation process, substantially all the phenol in the cyclohexylbenzene hydroperoxide cleavage effluent can be converted to cyclohexanone. In practice, however, depending on market conditions, there is likely to be a significant demand for phenol product. This can readily met using the present process by reliance on the reversible nature of the reaction (II), namely by dehydrogenating at least some of the cyclohexanone back to phenol. This can readily be achieved by, for example, contacting the cyclohexanone with a dehydrogenation catalyst, such as the promoted nickel catalyst described in U.S. Pat. No. 4,417,076. Preferably, such dehydrogenation is conducted at a temperature of about 250° C. to about 500° C. and/or a pressure of about 1 kPa to 200 kPa (approximately 0.01 atm to 20 atm).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cyclohexanone, the process comprising:
   (a) oxidizing cyclohexylbenzene to produce cyclohexylbenzene hydroperoxide;
   (b) converting cyclohexylbenzene hydroperoxide from (a) to produce an effluent stream comprising phenol and cyclohexanone;
   (c) feeding at least a portion of the effluent stream comprising phenol and cyclohexanone to at least one hydrogenation reaction zone; and
   (d) contacting the effluent stream portion with hydrogen in the presence of a hydrogenation catalyst in the hydrogenation reaction zone under conditions effective to convert at least part of the phenol in the effluent portion into cyclohexanone.

2. The process of claim 1, wherein the effluent stream portion fed to the hydrogenation reaction zone has the same composition as the effluent stream produced by the converting (b).

3. The process of claim 1 and further including subjecting the effluent stream produced by the converting (b) to at least one separation step such that the effluent stream portion fed to the hydrogenation reaction zone contains less cyclohexanone than the effluent stream produced by the converting (b).

4. The process of claim 3, wherein the effluent stream portion fed to the hydrogenation reaction zone contains less than 50 wt % cyclohexanone.

5. The process of claim 1, wherein the conditions in (d) comprise a temperature of from 20° C. to 250° C. and/or a pressure of from 101 kPa to 10,000 kPa and/or a hydrogen to phenol molar ratio of 1:1 to 100:1.

6. The process of claim 1, wherein the hydrogenation catalyst comprises platinum and/or palladium.

7. The process of claim 1 which further comprises a step of contacting benzene and hydrogen with a hydroalkylation catalyst under hydroalkylation conditions to produce the cyclohexylbenzene for oxidizing in (a).

8. The process of claim 7, wherein said the hydroalkylation catalyst comprises a molecular sieve of the MCM-22 family.

9. The process of claim 7, wherein the hydroalkylation conditions include a temperature of from 100° C. to 400° C. and/or a pressure of from 100 to 7,000 kPa and/or a molar ratio of hydrogen to benzene of from 0.15:1 to 15:1.

10. The process of claim 1, wherein at least a portion of the cyclohexanone product is contacted with a dehydrogenation catalyst under dehydrogenation conditions to convert the cyclohexanone to phenol.

11. A process for producing cyclohexanone, the process comprising:
   (a) oxidizing cyclohexylbenzene to produce cyclohexylbenzene hydroperoxide;
   (b) converting cyclohexylbenzene hydroperoxide from (a) to produce an effluent stream comprising phenol and cyclohexanone;
   (c) feeding at least a portion of the effluent stream comprising phenol and cyclohexanone to at least one hydrogenation reaction zone; and
   (d) contacting the effluent stream portion with hydrogen in the presence of a hydrogenation catalyst in the hydrogenation reaction zone under conditions effective to convert at least part of the phenol in the effluent portion into cyclohexanone wherein the effluent stream produced by the converting (b) is subjected to at least one separation step such that the effluent stream portion fed to the hydrogenation reaction zone contains less cyclohexanone than the effluent stream produced by the converting (b).

12. A process for producing cyclohexanone, the process comprising:
   (a) oxidizing cyclohexylbenzene to produce cyclohexylbenzene hydroperoxide;
   (b) converting cyclohexylbenzene hydroperoxide from (a) to produce an effluent stream comprising phenol and cyclohexanone;
   (c) feeding at least a portion of the effluent stream comprising phenol and cyclohexanone to at least one hydrogenation reaction zone; and
   (d) contacting the effluent stream portion with hydrogen in the presence of a hydrogenation catalyst in the hydrogenation reaction zone under conditions effective to convert at least part of the phenol in the effluent portion into cyclohexanone wherein the effluent stream portion fed to the hydrogenation reaction zone has the same composition as the effluent stream produced by the converting (b).

* * * * *